United States Patent

Hsien

[11] Patent Number: 5,279,310
[45] Date of Patent: Jan. 18, 1994

[54] SPINAL COLUMN CORRECTION DEVICE

[76] Inventor: Ching Chi Hsien, P.O. Box 82-144, Taipei, Taiwan

[21] Appl. No.: 9,218

[22] Filed: Jan. 26, 1993

[51] Int. Cl.$^5$ .................. A61G 15/00; A61F 5/00; A47G 9/00
[52] U.S. Cl. ................... 128/845; 602/32; 606/240; 128/DIG. 20; 5/636
[58] Field of Search ............... 128/845, 870; 602/5, 602/1, 12, 13, 16, 15, 19, 23, 24, 32, 33, 34, 35, 36, 38–40; 606/237–41; 5/636, 637, 648

[56] References Cited

U.S. PATENT DOCUMENTS

| | | | |
|---|---|---|---|
| 2,818,854 | 1/1958 | Johnson | 606/240 |
| 4,230,099 | 10/1980 | Richardson | 606/240 |
| 4,821,355 | 4/1989 | Burkhardt | 5/636 |
| 4,850,067 | 7/1989 | Latorre | 5/636 |
| 4,889,109 | 12/1989 | Gifford | 606/240 |
| 5,018,231 | 5/1991 | Wang | 5/636 |
| 5,070,865 | 12/1991 | Iams | 606/240 |
| 5,125,123 | 6/1992 | Engle | 5/648 |
| 5,180,386 | 1/1993 | Kennedy | 606/240 |

Primary Examiner—Michael A. Brown
Attorney, Agent, or Firm—Alfred Lei

[57] ABSTRACT

This invention relates to a spinal column correction device and in particular to one including a head rest having a first raised support, a second raised support formed with a recess at the intermediate portion, a groove between the first raised support and the second raised support, a triangular region extending downwardly from the second raised support, and a Velcro strap at the lower edge of the head rest, a lumbar rest having a Velcro strap at the upper edge and the lower edge, a swollen region at the intermediate portion, a spine line at the center, a triangular region at the upper portion, and two recesses at the lower portion for receiving two hips of an user, and a bottom rest having two recesses for receiving two feet of an user and a swollen region between the two recesses for resting the feet, whereby the device may effectively correct the spinal column of an user.

2 Claims, 5 Drawing Sheets

SPINAL COLUMN CORRECTION DEVICE

BACKGROUND OF THE INVENTION

The spinal column is bony column forming the main structural support of the skeleton of man and other vertebrates. It consists of segments (vertebrae) linked by flexible joints and held together by gelatinous disks of cartilage and by ligaments. In human beings, the spinal column of the child contains 33 vertebrae; the last 9 become fused into two immovable bones, the sacrum and the coccyx, forming the back of the pelvis, so that in the adult there are 26 separate bony segments. The 24 movable vertebrae are the 7 cervical (neck), 12 dorsal and 5 lumbar. Each vertebra has a somewhat cylindrical bony body, a number of wing-like projections, and a bony arch. The bodies of the vertebrae form the strong but pliable supporting column of the skeleton. The arches are positioned so that the space they enclose is in effect a tube, the neutral canal. It housed and protects the spinal cord and within it the spinal fluid circulates. Ligaments and muscles are attached to various projections of the vertebrae. The 12 pairs of ribs that make up the front of the chest are linked to the dorsal vertebrae. The spine is subject to curvature, injury, inflections, tumor formation, arthritic disorders, and puncture or slippage of the cartilage disks.

Therefore, it is an object of the present invention to provide a device which can correct the spinal column of an user.

SUMMARY OF THE INVENTION

This invention relates to a spine correction device.

It is the primary object of the present invention to provide a spine correction device which may be adjusted to adapt to the curve of the spine of an user.

It is another object of the present invention to provide a spine correction device which is safe in use.

It is still another object of the present invention to provide a spine correction device which is simple in construction.

It is still another object of the present invention to provide a spine correction device which is economic to produce.

It is a further object of the present invention to provide a spine correction device which is easy to assemble.

Other objects and merits and a fuller understanding of the present invention will be obtained by those having ordinary skill in the art when the following detailed description of the preferred embodiment is read in conjunction with the accompanying drawings.

DETAILED DESCRIPTION OF THE PREFERRED EMBODIMENT

Figure 1:
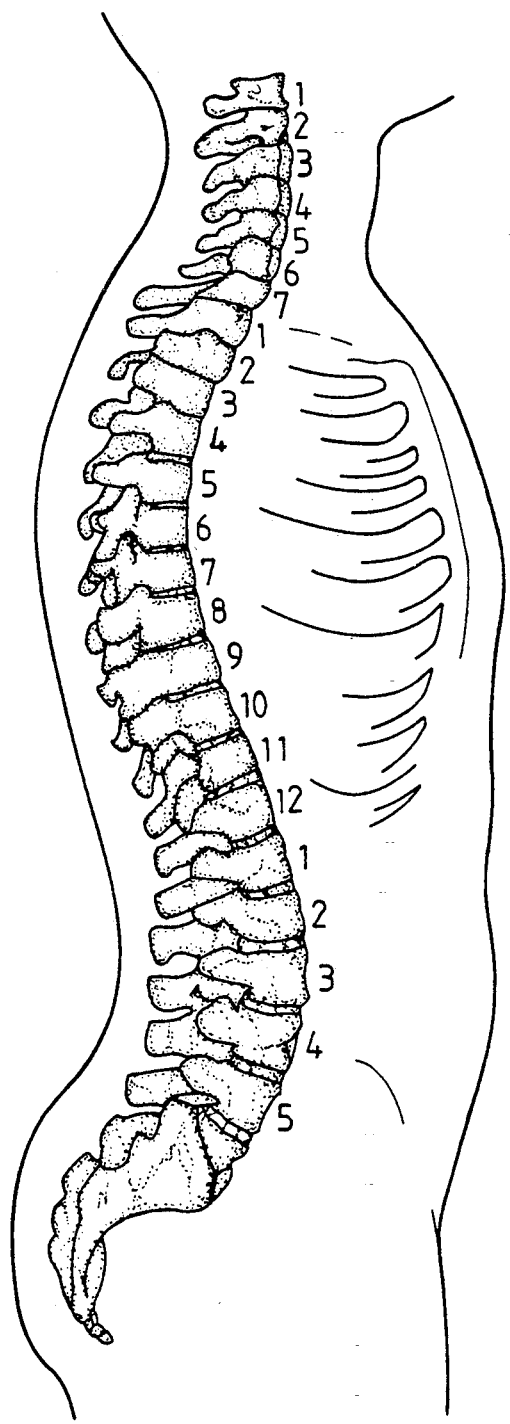
FIG. 1 shows the spinal column correction device of a human being.
Figure 2:
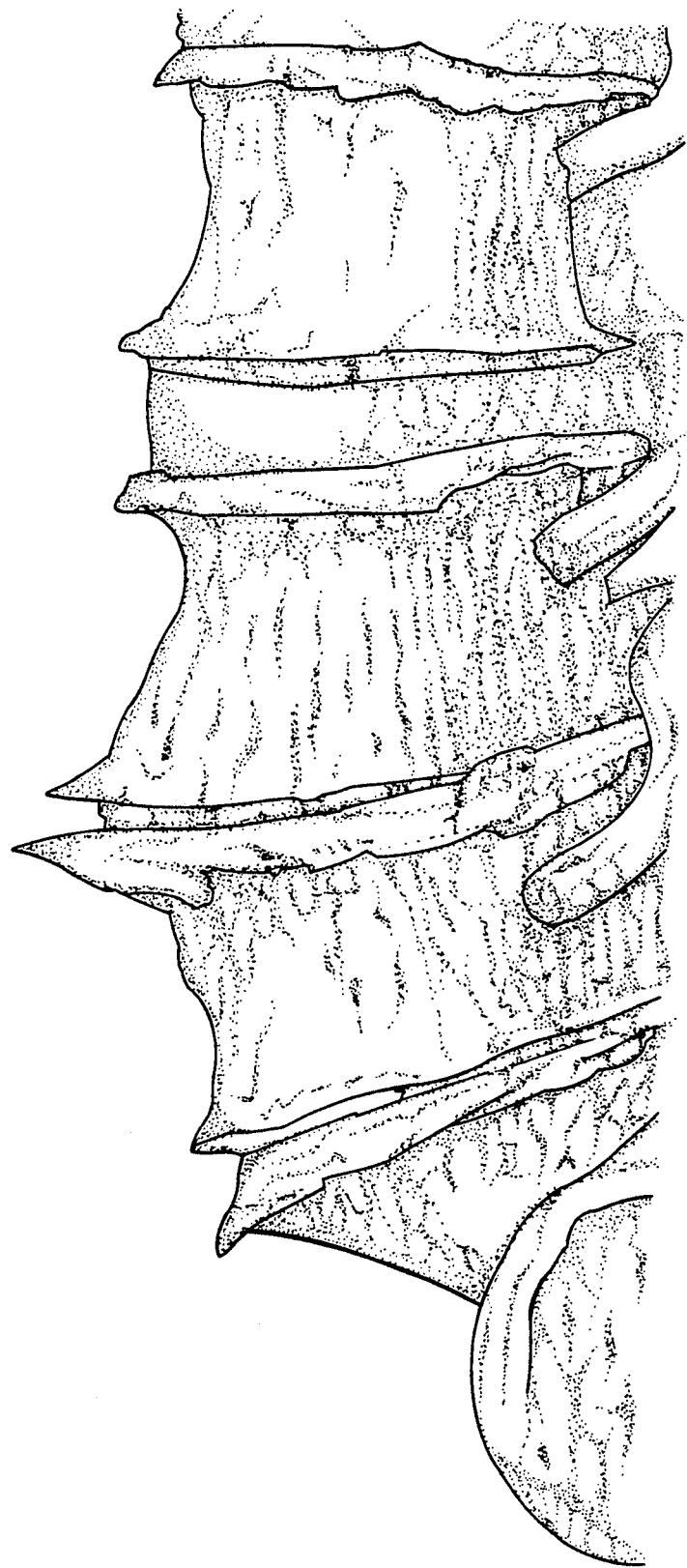
FIG. 2 shows the connection joint between two bones.

For purpose to promoting an understanding of the principles of the invention, reference will now be made to the embodiment illustrated in the drawings. Specific language will be used to describe same. It will, nevertheless, be understood that no limitation of the scope of the invention is thereby intended, such alternations and further modifications in the illustrated device, and such further applications of the principles of the invention as illustrated herein being contemplated as would normally occur to one skilled in the art to which the invention relates.

Figure 3:
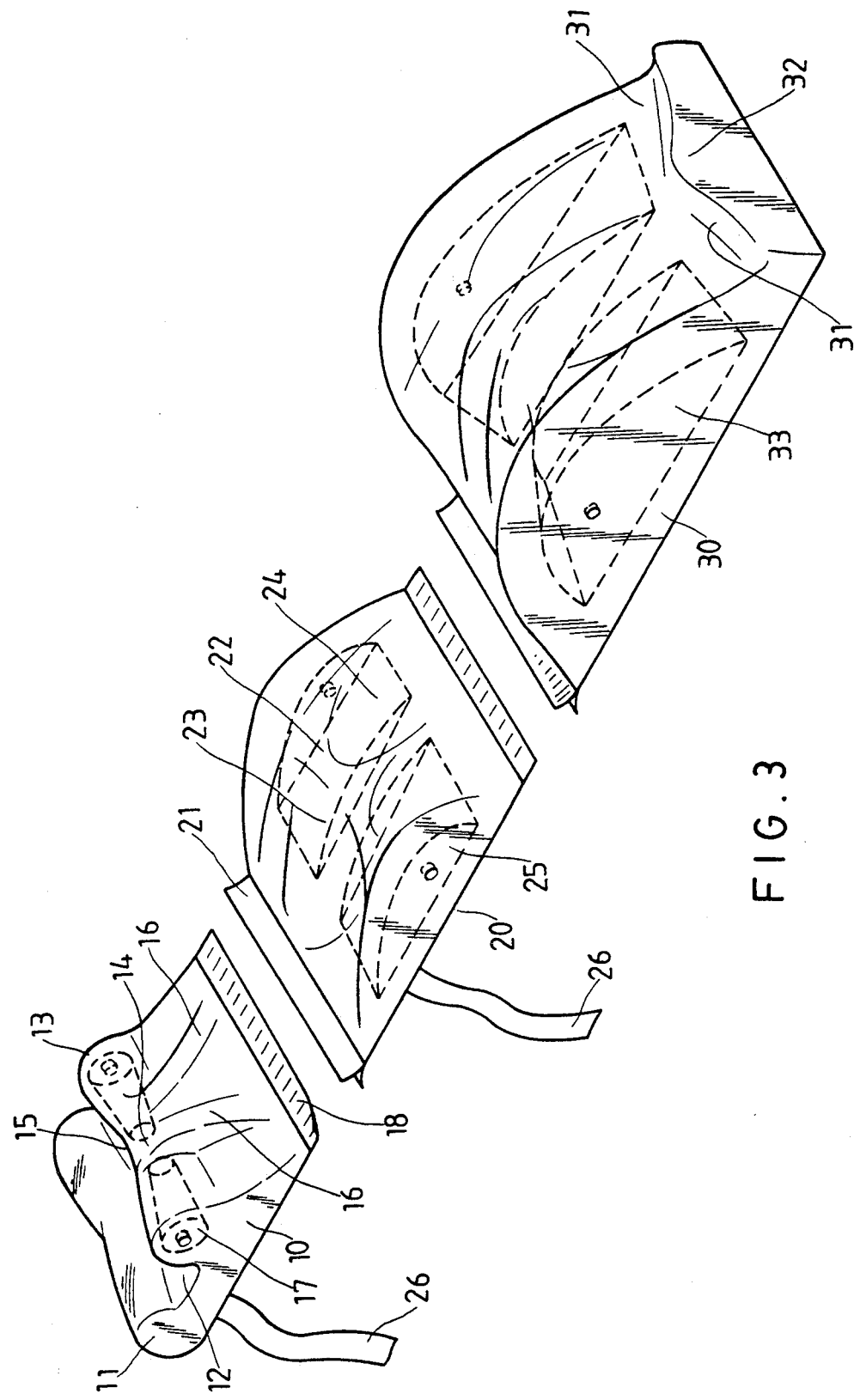
FIG. 3 is an exploded view of the present invention.
Figure 4:
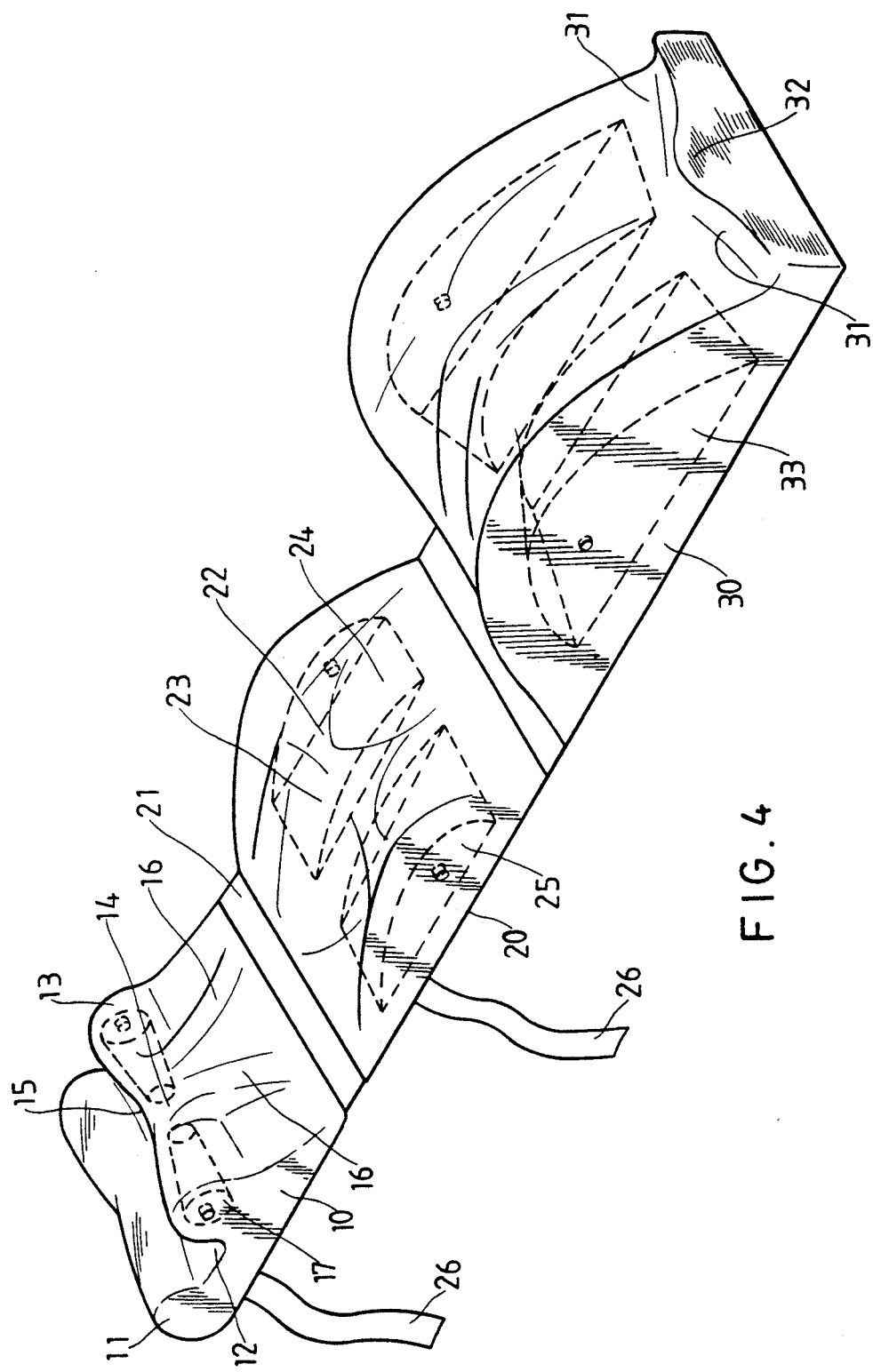
FIG. 4 is a perspective view of the present invention.
Figure 5:
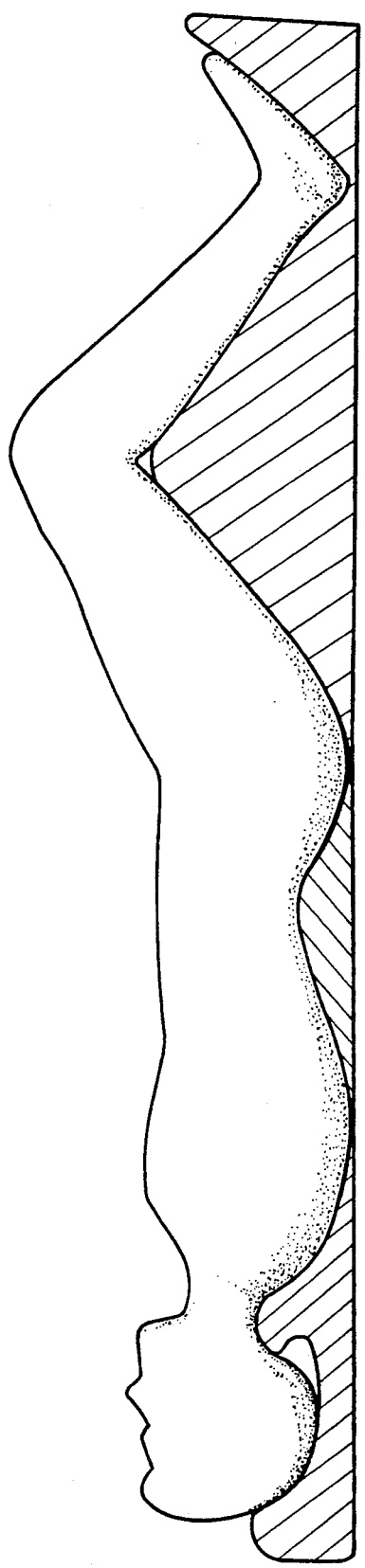
FIG. 5 is a working view of the present invention.

With reference to the drawings and in particular to FIGS. 3 and 4 thereof, the spinal column correction device according to the present invention mainly comprises a head rest 10, a lumbar rest 20, and a bottom rest 30. The head rest 10 is formed with a first raised support 11, a groove 12, a second raised support 13 with a recess 14 at the intermediate portion and a raised line 15, a triangular region 16 extending downwardly from the second raised support 13, an inflation chamber 17 at both ends of the second raised support 13, and a hook and loop strap 18 at the lower side of the head rest 10. When in use, the user's head is received in the groove 12 between the first raised support 11 and the second raised support 13, with his neck resting on the recess 14 of the second raised support 13.

The lumbar rest 20 includes a hook and loop strap 21 at upper side and the lower side, a spine line 22 at the center, a triangular region 23 at the upper portion, two recesses 24 at the lower portion for receiving the two hips of an user, and two inflation chambers 25 in the interior.

The bottom rest 30 is formed with two recesses 31 for receiving two feet of the user, a swollen portion 32 between the two recesses 31 for the rest of the feet, and two inflation chambers 30 within the bottom rest 30 for adjusting the height and hardness of the bottom rest 30.

Further, the head rest 10 and the lumbar rest 20 are provided with a strap 26 so that they can be bound on a seat or the like as desired.

When in use, the head rest 10, the lumbar rest 20, and the bottom rest 30 are connected together by engaging the hook and loop straps and then the inflation chambers are adjusted to adapt to the curve of the spine of the user.

The application of the present invention is too wide to be mentioned and cannot be all enumerated here in detail. It is understood that the present disclosure is made by way of example only and that numerous changes int the detail of construction and the combination of parts may be resorted to without departing from the spirit and scope of the invention as hereinafter claimed.

I claim:

1. A spinal column correction device comprising:
   a head rest having a first raised support, a second raised support formed with a recess at the intermediate portion, a groove between said first raised support and said second raised support, a triangular region extending downwardly from said second raised support, and a hook and loop strap at the lower edge of said head rest;
   a lumbar rest having a hook and loop strap at the upper edge and the lower edge, a spine line at the center, a triangular region at the upper portion, and two recesses at the lower portion for receiving two hips of an user; and
   a bottom rest having two recesses for receiving two feet of an user and a swollen region between the two recesses for resting the feet.

2. The spinal column correction device as claimed in claim 1, wherein the second raised portion of said head rest, the swollen region of said lumbar rest, and the swollen region of said bottom rest are provided with inflation chambers.

* * * * *